United States Patent
Fuhrman

(10) Patent No.: US 11,173,262 B2
(45) Date of Patent: Nov. 16, 2021

(54) DEVICE AND METHOD TO COMPENSATE FOR AIR LEAK FROM AN ANESTHESIA CIRCLE CIRCUIT

(71) Applicant: Texas Tech University System, Lubbock, TX (US)

(72) Inventor: Bradley P. Fuhrman, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 308 days.

(21) Appl. No.: 16/263,749

(22) Filed: Jan. 31, 2019

(65) Prior Publication Data

US 2020/0246565 A1    Aug. 6, 2020

(51) Int. Cl.
*A61M 16/00*    (2006.01)
*A61M 16/18*    (2006.01)
(Continued)

(52) U.S. Cl.
CPC ........ *A61M 16/0045* (2013.01); *A61M 16/18* (2013.01); *A61M 16/208* (2013.01); *A61M 16/22* (2013.01); *A61M 2202/0225* (2013.01); *A61M 2205/18* (2013.01); *A61M 2205/3337* (2013.01)

(58) Field of Classification Search
CPC .............. A61M 16/00; A61M 16/0045; A61M 16/0072; A61M 16/0074; A61M 16/0078; A61M 16/0081; A61M 16/01; A61M 16/0883; A61M 16/0891; A61M 16/18; A61M 16/201; A61M 16/208; A61M 16/22; A61M 2016/003; A61M 2016/0033; A62B 7/08
See application file for complete search history.

(56) References Cited

U.S. PATENT DOCUMENTS 4,510,930 A * 4/1985 Garcia ................... A62B 15/00
128/202.22
4,719,910 A    1/1988 Jensen
(Continued)

OTHER PUBLICATIONS

International Search Report and Written Opinion, PCT/US2020/015301 [ISA/US] dated Apr. 27, 2020.

*Primary Examiner* — Joseph D. Boecker
(74) *Attorney, Agent, or Firm* — Edwin S. Flores; Daniel J. Chalker; Chalker Flores, LLP

(57) ABSTRACT

The disclosure provides a way to supplement the tidal volume delivered to the patient by a leaking re-breather when the delivered volume becomes less than that set by the ventilator (in either pressure-regulated or volume modes). This may be accomplished with a shunt—a gas conduit joining the non-patient side of the re-breather to the patient side. A low-resistance, plenum or a draw-over vaporizer may also be incorporated into the gas pathway. Such a device may include a housing with a movable partition separating an actuating side from a patient side. The housing includes a ventilator orifice for pneumatic communication between a ventilator and the actuating side and a patient orifice for pneumatic communication between the patient side and a patient. A shunt defines a bypass flow path from the actuating side and to the patient side when the moveable partition is at a maximal displacement towards the patient side.

17 Claims, 11 Drawing Sheets

(51) Int. Cl.
*A61M 16/22* (2006.01)
*A61M 16/20* (2006.01)

(56) References Cited

U.S. PATENT DOCUMENTS

| | | | |
|---|---|---|---|
| 5,678,540 A | 10/1997 | Kock et al. | |
| 6,123,072 A * | 9/2000 | Downs | A61M 16/00 |
| | | | 128/204.21 |
| 2003/0015199 A1 * | 1/2003 | Fuhrman | A61M 16/104 |
| | | | 128/204.18 |
| 2003/0208131 A1 | 11/2003 | George | |
| 2004/0118402 A1 | 6/2004 | Heinonen | |
| 2005/0076911 A1 * | 4/2005 | Fuhrman | A61M 16/01 |
| | | | 128/205.12 |
| 2006/0107947 A1 * | 5/2006 | Rist | A61M 11/00 |
| | | | 128/200.14 |
| 2008/0276940 A1 | 11/2008 | Fuhrman et al. | |
| 2009/0050151 A1 * | 2/2009 | Fuhrman | A61M 16/0081 |
| | | | 128/204.21 |

\* cited by examiner

DEVICE AND METHOD TO COMPENSATE FOR AIR LEAK FROM AN ANESTHESIA CIRCLE CIRCUIT

CROSS-REFERENCE TO RELATED APPLICATIONS

None.

FIELD OF THE DISCLOSURE

The present invention relates to anesthesia machines and other rebreathing devices which typically separate two gas flow systems, one a circuit of gas flow comprised of patient inspired and expired air and the other, a separate system of air flow that powers or facilitates breathing. Embodiments of this invention are methods, systems and devices to compensate for loss of gas volume on the patient side of such an anesthesia machine.

STATEMENT OF FEDERALLY FUNDED RESEARCH

None.

BACKGROUND OF THE DISCLOSURE

Anesthesia machines and other rebreathing devices may comprise a chamber divided into a patient side and a non-patient side by a moveable partition, typically a bellows. When a ventilator pumps air into the non-patient side of the chamber, the partition is moved, displacing air from the patient side of the chamber into the patient's lungs. Thus, the ventilator powers breathing without air from the ventilator (non-patient, or "actuating" side) reaching the patient. Fresh gas may be continuously infused into the patient side to replenish oxygen, anesthetic may be provided to the patient air, and a scrubber may be used to absorb carbon dioxide from the patient exhaled gas.

When incidental leakage of air from the patient side of the system reduces the volume of air on the patient side of the partition (lung, tubing and bellows volumes), the remaining volume may prove insufficient for the patient side of the device to deliver a complete next breath. This may result in the breath to the patient being smaller than intended even if delivery of a tidal volume of gas to the non-patient side causes a maximal displacement of the partition, virtually emptying the patient side of the chamber.

Such leakage may occur because the endotracheal tube is too narrow to seal the airway, because of rupture of the endotracheal tube cuff, because of rupture of the lung and drainage of pleural air by tube thoracostomy, as a result of airway suctioning during nursing care, because of transient patient disconnect from the anesthesia machine, because of inadequate seal of a mask or laryngeal mask airway, or other reasons.

This leakage, if not compensated, could result in inadequate tidal volume and inadequate ventilation of the patient with consequent hypoxemia, hypercarbia or even asphyxia. It might result in inadequate lung inflation and loss of residual lung volume with consequent atelectasis, ventilation perfusion mismatch, and hypoxemia. These consequences are potentially lethal.

Anesthesia machines require constant attention and continuous monitoring of adequacy of breathing to protect against these adverse effects. An excessive leak causes the anesthesia machine to alarm, and the responsible attendant, almost immediately, manually bleeds supplemental fresh gas, generally containing no anesthetic, into the patient side of the re-breather. This manual process interrupts the attendant's other work flow, requires continuous presence of the attendant, and, unless the fresh gas contains anesthetic, may reduce anesthetic concentration delivered to the patient.

There are distinct advantages to the use of inhaled anesthetic agents as sedatives in the intensive care unit including precision of dosing, rapid onset and cessation of effect, virtual absence of tachyphylaxis, potent bronchial relaxation, proposed beneficial effects on reperfusion injury, and low cost. However, in the intensive care unit (ICU) environment, the need for continuous attention to the anesthetic machine by an appropriately trained attendant limits these opportunities.

The present disclosure provides techniques to automatically compensate for leaks from the patient side of an anesthetic re-breather, to allow time for a delay in response by the attendant. It alerts the attendant that compensation for a leak is required, that a leak exists perhaps requiring its elimination, and to maintain continuous sedation or anesthesia despite such a leak.

BRIEF SUMMARY OF THE DISCLOSURE

The disclosure provides a way to supplement the tidal volume delivered to the patient by a leaking re-breather when the delivered volume becomes less than that set by the ventilator (in either pressure-regulated or volume modes). In a first embodiment, this is accomplished with a shunt—a gas conduit joining the non-patient side of the re-breather to the patient side. A low-resistance vaporizer may also be incorporated into the gas pathway.

In a first aspect, the present disclosure may be embodied as a rebreathing device. The device includes a movable partition having an actuating side on a first side of the movable partition, and a patient side on a second side of the movable partition. A housing is disposed about the movable partition (e.g., the movable partition divides the housing into a patient side and an actuating side). The moveable partition is capable of being moved (e.g., displaced) towards either the patient side or the actuating side. The housing includes a ventilator orifice for pneumatic communication between a ventilator and the actuating side. The housing also includes one or two patient orifices for pneumatic communication between the patient side and a patient. A shunt defines a bypass flow path from the actuating side and to the patient side when the moveable partition is at a maximal displacement towards the patient side. In some embodiments, the shunt is blocked during normal operation and unblocked when patient side is maximally evacuated to allow fluid flow from the actuating side to the patient side.

The rebreathing device may further have a vaporizer disposed in the bypass flow path of the shunt. The vaporizer may include a fresh gas orifice for receiving fresh gas and providing same to the patient side. The bypass flow path of the shunt may further include a $CO_2$ scrubber. A patient return orifice may be in pneumatic communication with the patient side by way of the $CO_2$ scrubber.

The shunt may include a valve disposed in the bypass flow path to prevent fluid flow from the patient side to the actuating side. The valve may be a check valve. The valve may be a starling resistor configured to permit fluid flow to a vaporizer when a pressure on the patient side is less than a pressure on the actuating side. The shunt may further include a check valve disposed in the bypass flow path between the vaporizer and the patient side.

In some embodiments, the shunt includes a flow meter. In some embodiments, the shunt includes a flow alarm. The flow alarm may be a whistle.

The rebreathing device may further include an exhaust conduit defining an exhaust flow path from the patient side. The exhaust conduit may have a starling resistor configured to permit an exhaust flow from the patient side when a pressure on the patient side is greater than a pressure on the actuating side. The exhaust conduit may further include an exhaust valve disposed in the exhaust flow path between the patient side and the starling resistor. The exhaust valve may be configured to permit an exhaust gas flow when the pressure drop across the exhaust valve is greater than the pressure caused by the weight of the moveable partition alone.

In another aspect, the present disclosure may be embodied as a method for leak compensation in a rebreather. The method includes providing a rebreathing device having a movable partition for causing a gas flow in a patient side of the rebreathing device in response to gas flow on an actuating side of the rebreathing device. A gas flow is provided on the actuating side to cause displacement of the moveable partition towards the patient side thereby causing a gas flow from the patient side. If the moveable partition reaches a maximum displacement towards the patient side, a bypass gas is caused to flow from the actuating side to the patient side, bypassing the moveable partition. The method may further include preventing a bypass gas flow if the moveable partition is not maximally displaced towards the patient side. An anesthetic vaporizer may be provided between the patient side and a patient for providing anesthetic to the patient by way of the gas flow.

DESCRIPTION OF THE DRAWINGS

For a more complete understanding of the features and advantages of the present invention, reference is now made to the detailed description of the invention along with the accompanying figures and in which.

DETAILED DESCRIPTION OF THE DISCLOSURE

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Figure 1:
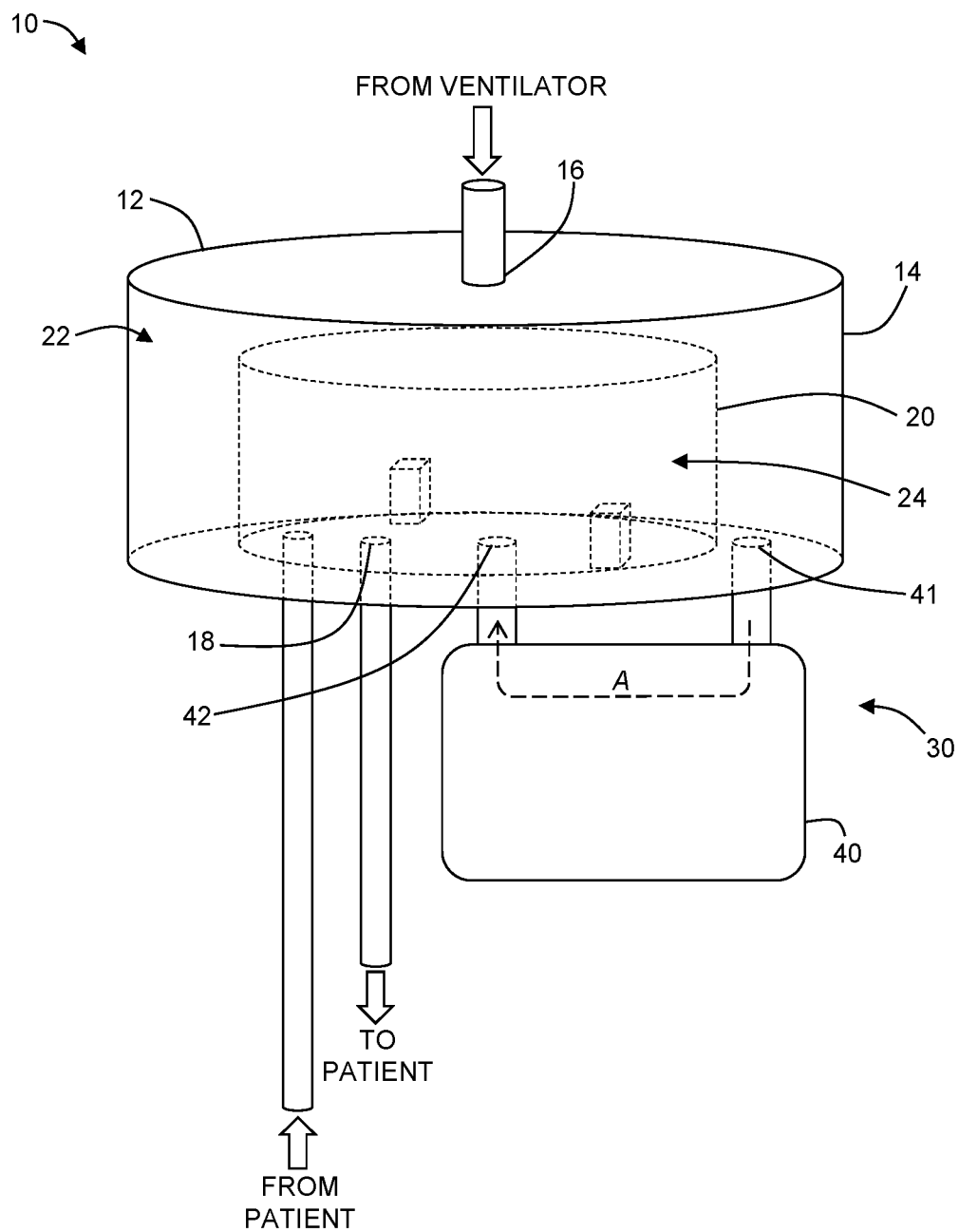
FIG. 1 is a diagram depicting a rebreathing device according to an embodiment of the present disclosure.

With reference to FIG. 1, the present disclosure may be embodied as a rebreathing device 10. The rebreathing device 10 includes a moveable partition 20 disposed in a housing 12. For example, the housing 12 may have a chamber 14 separated by the moveable partition 20. The moveable partition 20 has an actuating side 22 and a patient side 24. For example, where the moveable partition 20 separates sides of a chamber 14, the moveable partition 20 separates the chamber 14 into an actuating side 22 and a patient side 24. The moveable partition 20 may be of any suitable configuration, such as, for example, a bellows, a bag, a vane, etc. (examples herein refer to a bellows for convenience only and are not intended to limit the scope of the present disclosure).

The housing 12 has a ventilator orifice 16 for pneumatic communication between the actuating side 22 and a ventilator or similar device. In this way, for example, a ventilator may cause a flow cycling into and out of the actuating side 22 of the housing 12. The housing 12 also has a patient orifice 18 for pneumatic communication between the patient side 24 and a patient. For example, the patient orifice 18 may be in communication with an endotracheal tube disposed in a patient's airway. As gas flow enters the actuating side 22, the moveable partition 20 is moved towards the patient side 24 thereby causing a gas flow from the patient side 24 to the patient (inspiratory flow). As gas flows out from the actuating side 22 to the ventilator in expiration, the moveable partition 20 moves toward the actuating side 22 thereby allowing gas to flow from the patient to the patient side 24 (expiratory flow). It should be understood that other factors may influence gas flow and movement of the partition 20, including, for example, spontaneous breathing of the patient. It should also be understood that other components of the anesthesia circle circuit and anesthesia system (e.g., anesthetic vaporizer, $CO_2$ scrubber, fresh gas inflow system and regulator) may also be in pneumatic continuity with the patient side of the circuit.

As described above, leakage of gas on the patient side 24 (including from any components in pneumatic communication with the patient side 24) will cause a reduction in the volume of gas on the patient side 24 and therefore movement of the partition 20 may be displaced towards the patient side 24 due to the reduced volume. As such, the moveable partition 20 may reach a maximum displacement during inspiratory flow where continued gas flow into the actuating side 22 is prevented and will not cause further flow from the patient side 24 to the patient.

To compensate for such leakage, the rebreathing device 10 comprises a shunt 30 which defines a bypass flow path (shown by the arrow 'A') from the actuating side 22 to the patient side 24. In this way, a bypass flow of gas is caused to flow from the actuating side 22 to the patient side 24 if the moveable partition 20 is at a maximal displacement towards the patient side 22. A vaporizer 40 may be disposed in the bypass flow path of the shunt 30 to provide anesthetic gas to the patient. The vaporizer 40 may be, for example, a low-resistance or a drawover style vaporizer disposed such that gas may be pushed through it. Other forms of low resistance vaporizer or anesthetic nebulizer may be envisioned.

Further illustration is provided using a typical configuration where the moveable partition is a bellows which descends during inspiration. During descent of the bellows (inspiration) there is, in theory, little or no pressure drop across the partition, so the shunt has nearly equal inlet 41 (actuating side) and outlet 42 (patient side) pressures. The vaporizer is non-compliant, so, during delivery of gas to the chamber by a ventilator, there is no cause for flow through the shunt. Gas would flow, as the bellows descends, from the patient side of the rebreathing device into the patient's lungs because the lungs are compliant and expand under pressure, and because there is a pressure drop from the patient side of the chamber to the alveolus during air flow through the patient's bronchi.

In such a typical configuration, the weight of the upright bellows contributes to pressure on the patient side making the patient-side pressure slightly greater than the actuating-sider pressure. This partition weight may be designed so as to create a predetermined magnitude of pressure difference between the patient side and the actuating side. This predetermined pressure difference may be selected to assure there is no forward flow through the shunt (i.e., actuating side to the patient side) until descent of the bellows is halted due to maximal displacement. For example, if the bellows has a surface area of 300 cm$^2$, (approximately 7.5 inches in diameter), and the weight of the bellows is 150 g (approximately 5 ounces), then the bellows would add 0.5 g/cm$^2$ (approximately 0.5 cm H$_2$O) of pressure to the patient side. This pressure difference (the "partition pressure") would oppose forward flow through the shunt from actuating side to patient side. Other techniques to create such a "partition pressure" will be apparent in light of the present disclosure, such as, for example, the use of springs or elastic components.

Figure 2:
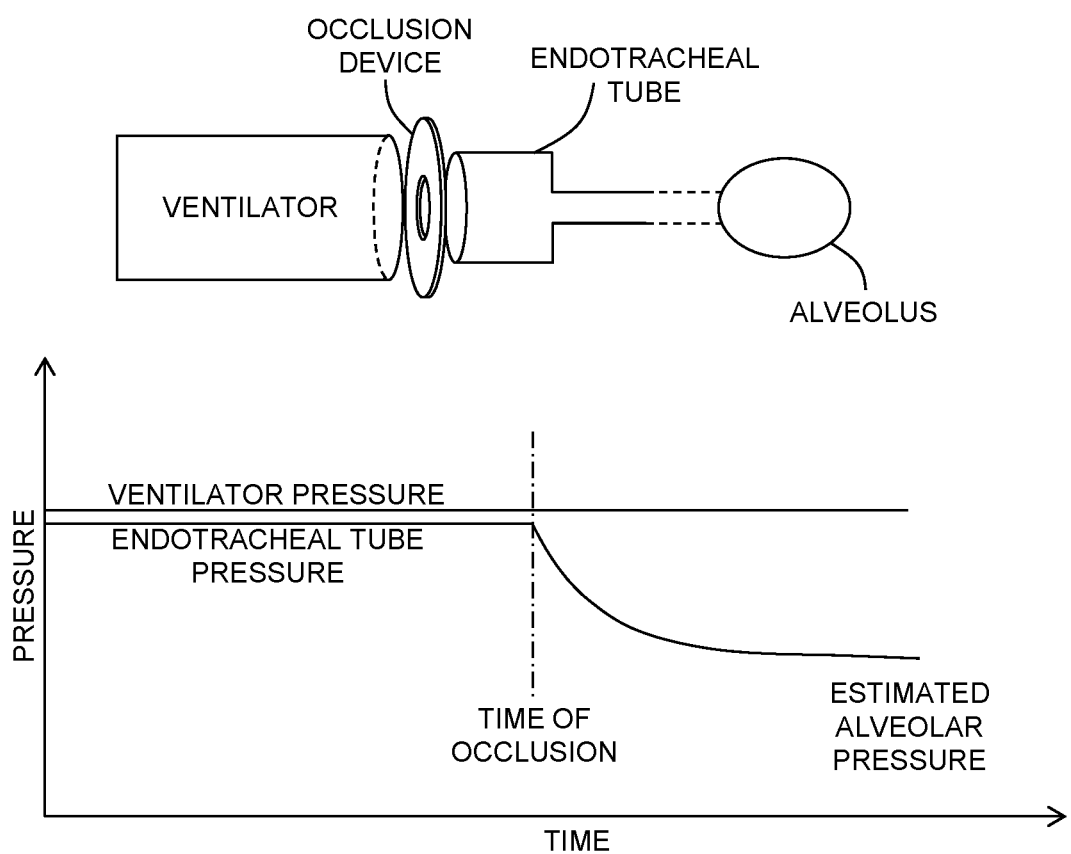
FIG. 2 illustrates ventilator and endotracheal tube pressures on occlusion of air flow during positive pressure inspiration.

During the inspiratory phase of positive pressure mechanical ventilation, a pressure drop from the patient side 24 of the rebreathing device 10 to the alveolus is close to the pressure drop from the ventilator to alveolus. This pressure drop is due to air flow across the resistance of an endotracheal tube, tracheostomy tube or airways within the lungs (illustrated in FIG. 2). If the pathway from the ventilator to the endotracheal tube is abruptly occluded, flow ceases and pressure in the endotracheal tube falls until it equals the downstream alveolar pressure. This pressure difference between the ventilator and the alveolus is the driving pressure that acts to push air through airways into the lungs during positive pressure mechanical ventilation.

Figure 3:
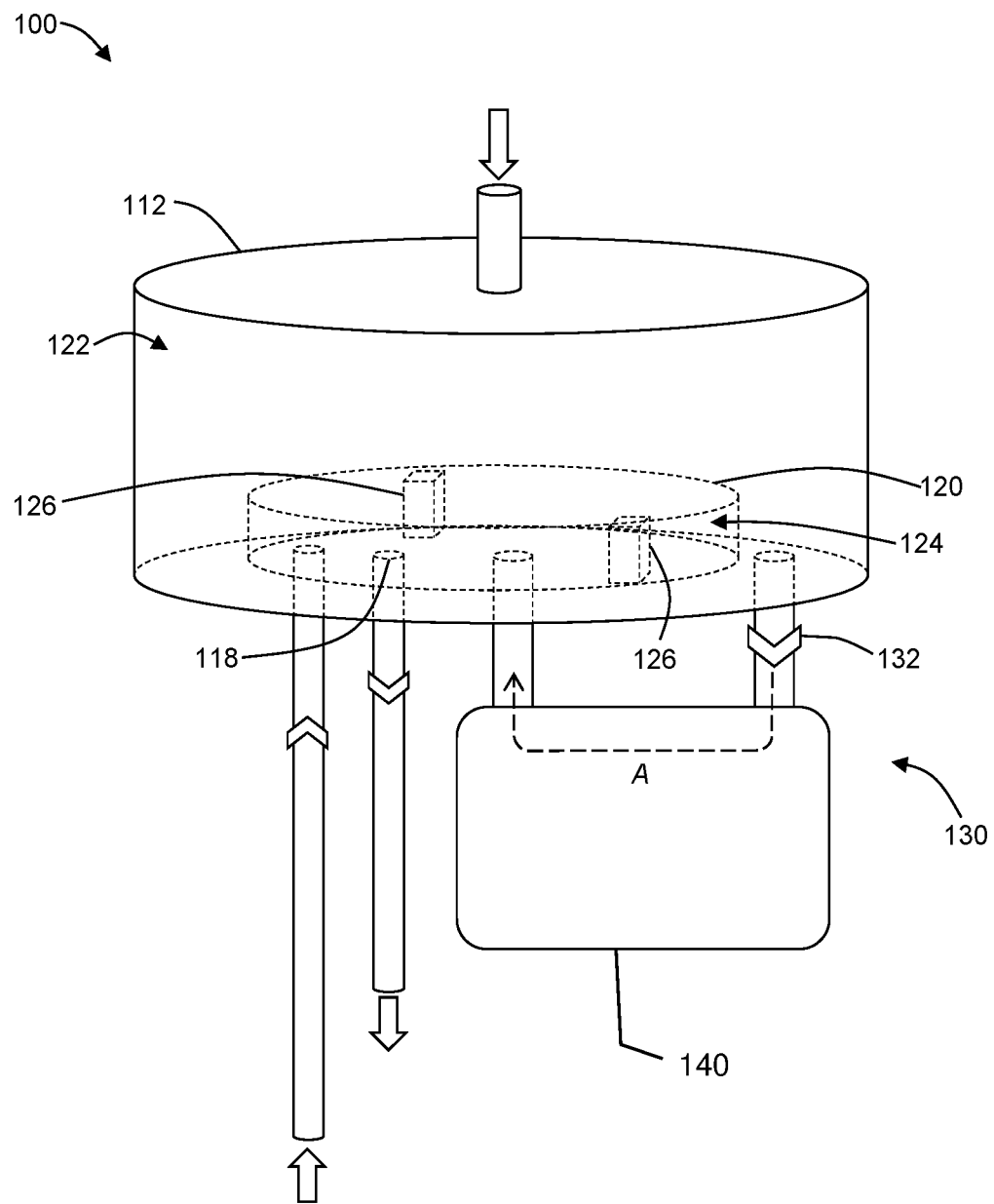
FIG. 3 is a diagram depicting a rebreathing device according to another embodiment of the present disclosure, wherein the moveable partition is shown at a maximum displacement toward the patient side.

When a volume of gas on the patient side is inadequate (e.g., resulting from a leak on the patient side), the moveable partition will reach a maximum displacement in the midst of inspiration. For example, in the exemplary bellows embodiment described above, the bellows will cease to descend when it is halted either by striking its own piled pleats or by striking a deliberately placed mechanical "stop." In embodiments with a stop, for example, as depicted in FIG. 3, when the moveable partition 120 hits the stop 126, the moveable partition 120 is maximally displaced toward the patient side 124 and the patient side 124 is maximally evacuated. Flow through airways transiently diminishes or ceases as air redistributes within the lung (toward the alveoli) and pressure on the patient side 124 falls toward alveolar pressure. The pressure of gas entering the shunt 130 (i.e., from the actuating side 122) then exceeds a downstream pressure at the patient side of the shunt 130, which itself exceeds the pressure in alveoli. This pressure difference creates a bypass flow through the shunt 130 from the actuating side 122 to the patient side 124 and, from there, to the expanding lungs. In this way, gas flows through the shunt 130 only when patient inspiration is interrupted by cessation of descent of the bellows 120.

FIG. 3 also shows an embodiment of a rebreathing device 100 wherein the shunt 130 has a valve 132 disposed in the bypass flow path. The valve 132 is configured so as to prevent a fluid flow from the patient side 124 to the actuating side 122 (i.e., reverse flow). For example, the valve 132 may be a check valve to provide flow in only the forward direction through the shunt 130. In this way, the rebreathing device 100 may operate as an anesthesia machine—the partition 120 having descended to the stops 126, ventilator air now passes through the shunt 130, picks up anesthetic from the vaporizer 140, returns to the patient side 124 of the housing 112 and then passes through the patient orifice 118 to the lungs of the patient. Retrograde flow through the shunt 130 is prevented at all times by the check valve 132. The check valve 132 may be placed in either the vaporizer's inflow or outflow positions to allow only forward flow from the actuating side 122 to the patient side 124. In some embodiments, check valve 132 may be configured to allow flow only when there is a pressure drop across it, which may be as low as a fraction of a centimeter of water.

Figure 4:
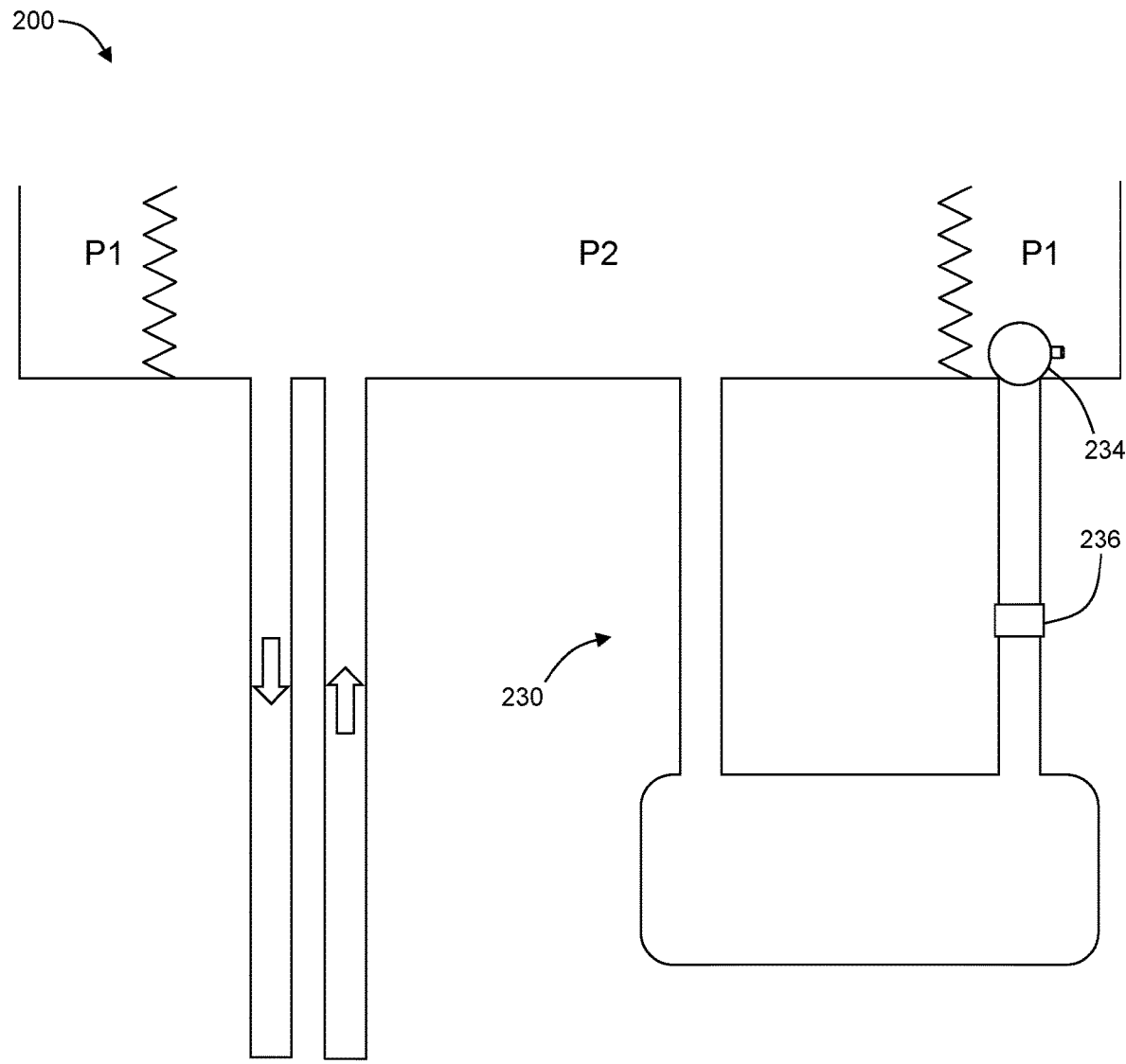
FIG. 4 is a diagram depicting a portion of a rebreathing device according to another embodiment of the present disclosure incorporating a whistle flow alarm.

FIG. 4 shows another embodiment of a rebreathing device 200 according to the present disclosure. The shunt 230 of this embodiment includes a whistle 234 whistle disposed in the bypass flow path. In this way, a bypass flow of gas through the shunt 230 will sound the whistle 234 thereby alerting an attendant to flow and signaling existence of a leak requiring attention. Other flow alarms, instead of or in addition to a whistle 234, may be provided. Some embodiments of a rebreathing device 210 may include a flow meter 236 provided within the shunt 230.

Figure 5:
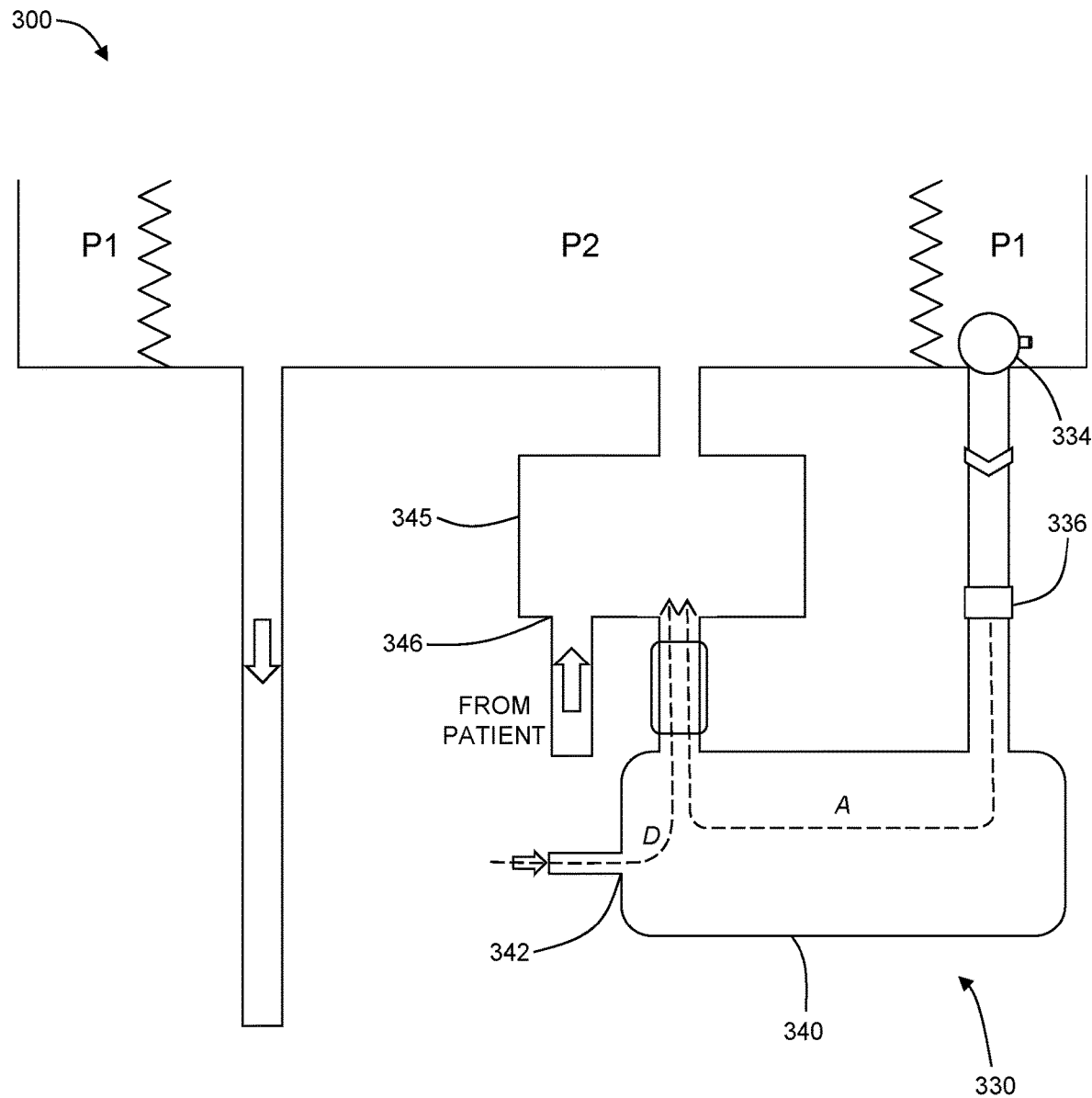
FIG. 5 is a diagram depicting a portion of a rebreathing device according to another embodiment of the present disclosure having a vaporizer.

FIG. 5 shows another embodiment of a rebreathing device 300 that may be used as an anesthesia machine, wherein a shunt 330 includes a vaporizer 340 disposed in the bypass flow path. The vaporizer 340 may have a fresh gas orifice 342 for providing fresh gas to the patient side. In this way, the vaporizer 340 may instill anesthetic into both the fresh gas flow (FGF) path (identified as 'D') and the bypass flow path (A). The vaporizer 340 may be used to continuously provide anesthetic to the rebreather 300. A CO$_2$ scrubber 345 may reside in fluid continuity with the patient expired air pathway and function as a part of the shunt 330. In some embodiments, the bypass flow path of the shunt 330 includes a CO₂ scrubber 345 with a patient return orifice 346. In this way, the patient return orifice 346 is in pneumatic communication with the patient side by way of the CO₂ scrubber 345.

Figure 6A:
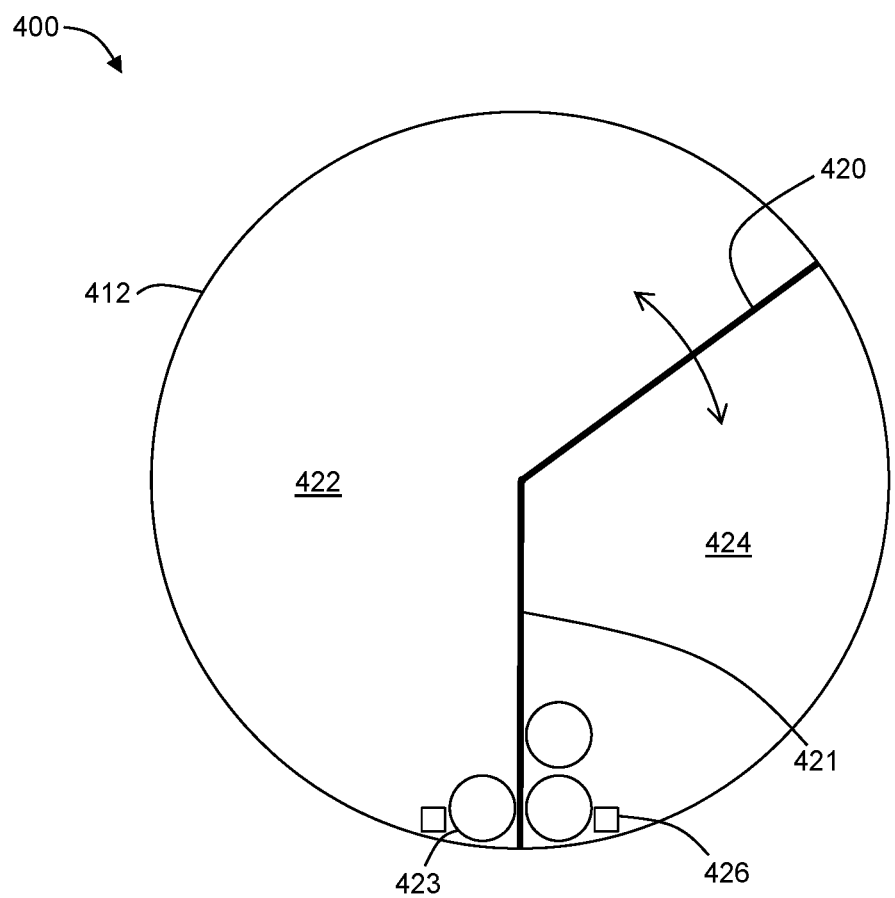
FIG. 6A is a top view of a housing an moveable partition of another rebreathing device according to the present disclosure.
Figure 6B:
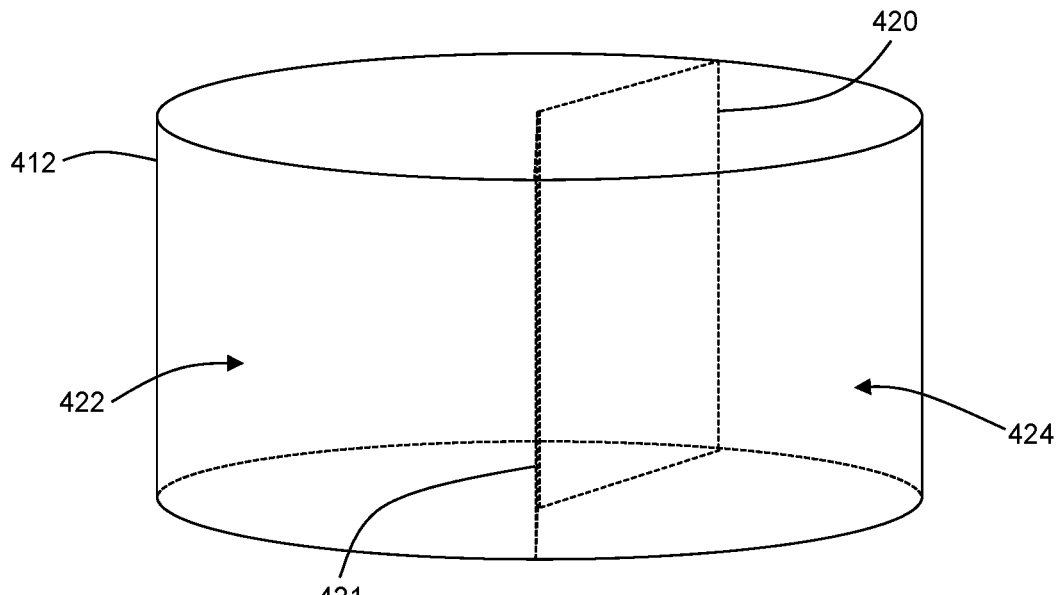
FIG. 6B is a perspective view of the housing and moveable partition of FIG. 6A.

FIGS. 6A and 6B illustrate an example of another embodiment of the present disclosure in which a rebreathing device 400 is configured as a "partial separator." Such an embodiment includes a moveable partition which comprises a "sail" 420 and a fixed partition 421. In such embodiments, patient and actuating sides of the rebreathing device 400 are separated by the sail 420 which is freely rotatable within the housing 412. The sail 420 may approach the fixed portion 421 of the partition from either direction. Positive pressure ventilation delivers gas to the actuating side 422 by way of ventilator port 423 and pushes the sail 420 toward a stop 426 on the patient side 424 of the housing 412. When the sail 420 abuts the stop 426, no further gas can be displaced toward the patient and the remainder of the intended ventilator breath is aborted.

Figure 7A:
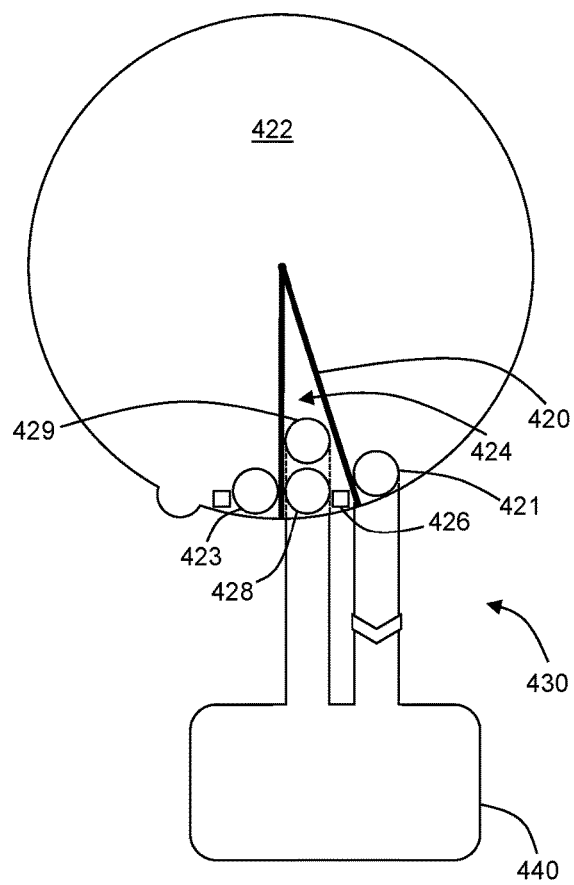
FIG. 7A depicts a rebreather according to another embodiment of the present disclosure.
Figure 7B:
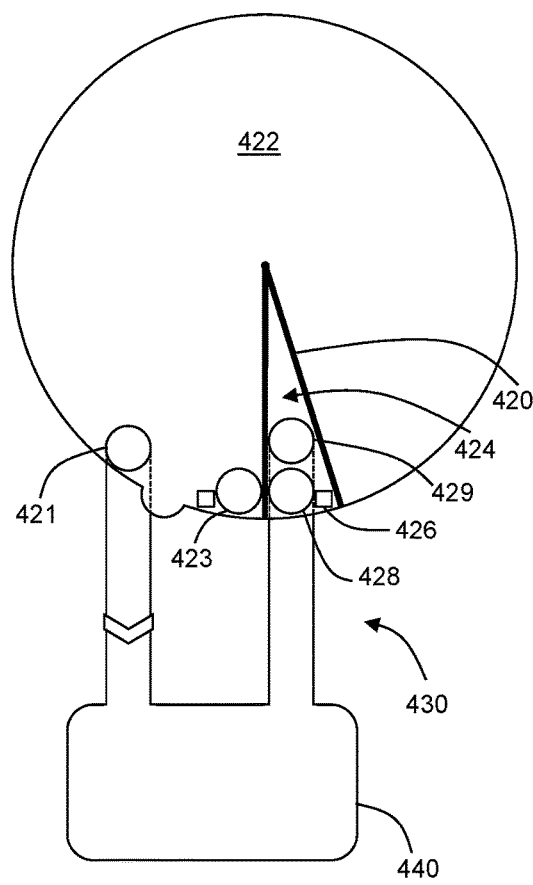
FIG. 7B depicts a rebreather according to another embodiment of the present disclosure.

FIGS. 7A and 7B show placement of a shunt 430 which includes a vaporizer 440 as described above with an inflow orifice 421 positioned such that it lies on the actuating side 422 of the partition 420 when the sail 420 abuts the patient side stop 426, and with an outflow orifice 428 positioned on the patient side 424 when the sail 420 abuts the patient side stop 426. This shunt 430 serves the same functions as described above (FIG. 3). Note from the figures that, during inspiration, shunt inflow and return pressures are equal except when the sail 420 abuts the patient side stop 426, allowing patient side pressure to drop toward alveolar pressure. When the sail 420 is in any other position, those pressures are equal and there is no flow through the shunt 430. The patient orifice 429 of the rebreather is positioned to receive gas either from the patient side of the rebreather 424 or from the shunt 428 outflow orifice 428.

Figure 8:
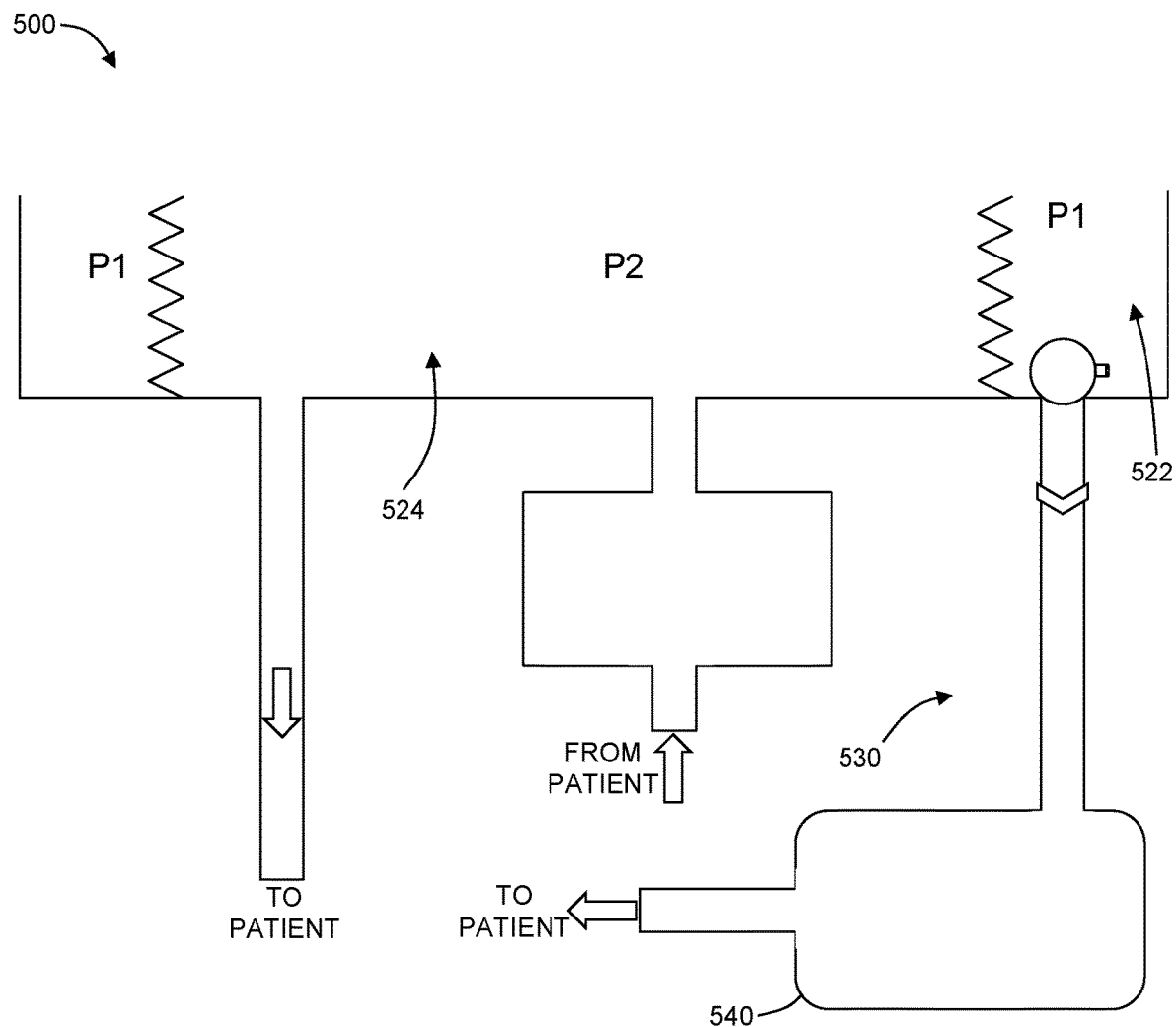
FIG. 8 depicts a portion of a rebreather according to another embodiment of the present disclosure where a shunt is configured to be in communication with a patient's airway.
Figure 9:
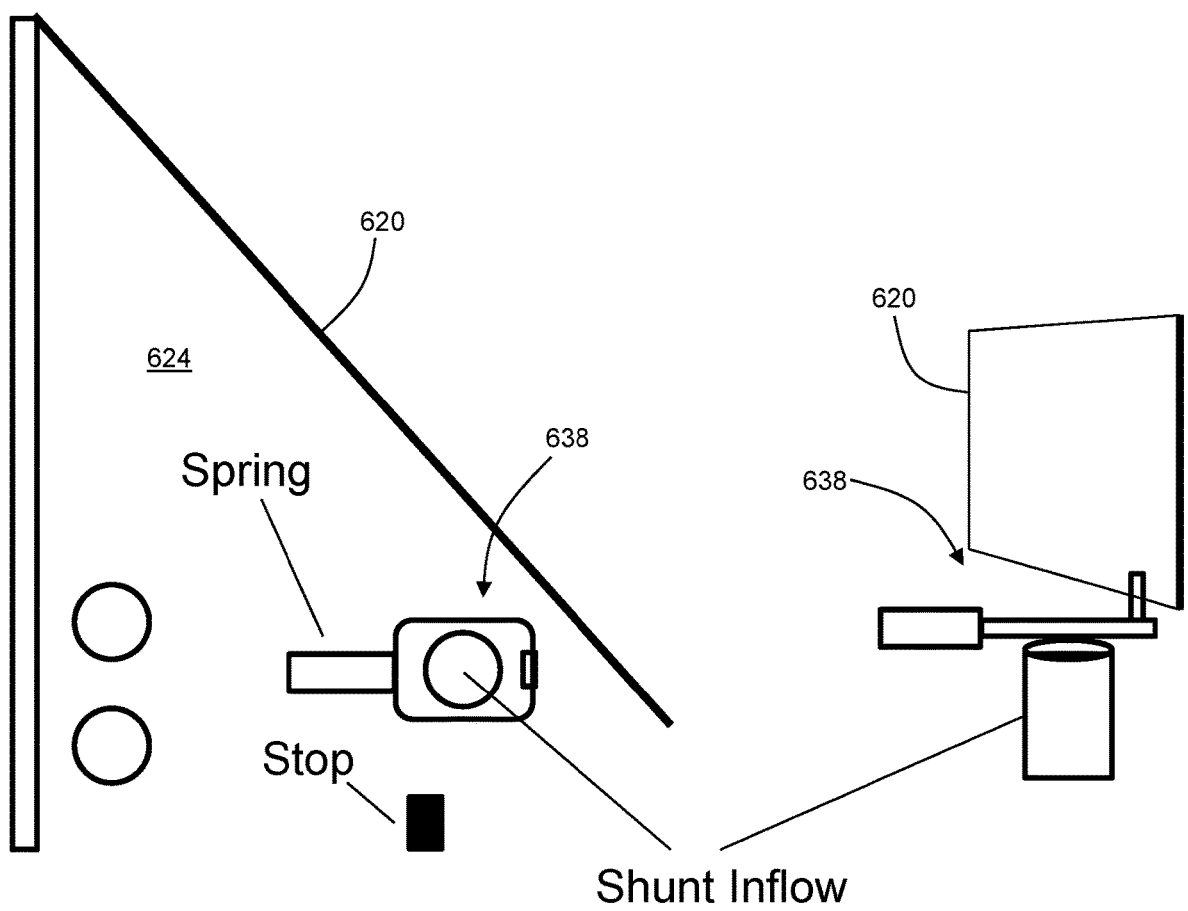
FIG. 9 depicts a portion of a device where flow through a shunt is controlled by a latch.

By connecting the actuating side 422 of the housing 412 to the patient side 424, the shunt 430 provides a bypass flow path by which a part of a tidal breath that cannot further displace the sail 420 may take up anesthetic and reach the patient (function 1). A shunt 430 disposed in this manner admits no bypass flow when the sail 420 is not in contact with the stop 426 (function 2). Alternatively, FIG. 8 depicts a system wherein function 1 can be accomplished by connecting the shunt 530 from the actuating side 522, through the vaporizer 540, directly to the patient's airway (see, e.g., FIG. 8), but this alternative does not accomplish function 2. Because the patient's lungs are distensible, positive pressure delivered by the ventilator would flow through such a shunt 530 throughout the inspiratory phase of mechanical ventilation, whether or not a leak existed. Such a bypass flow path is disadvantageous as it functionally adds to the circle circuit fresh gas flow in an uncontrolled fashion even when there is no leak. Patient metabolism produces carbon dioxide which is chemically exchanged by the scrubber material for water and water vapor. This provides humidification to the anesthesia circle circuit. Small patients produce small quantities of carbon dioxide. Excessive fresh gas flow in small patients therefore will reduce humidity and desiccate the patient's airways. To resolve such a continuous flow, FIG. 9 depicts a portion of a rebreathing device wherein continuous bypass flow through a shunt 630 is prevented by placement of a latch 638 that occludes the shunt inflow until the latch is released when the patient side 624 is maximally evacuated (i.e., when the sail 620 releases the latch 638 at the maximum displacement).

Low resistance (draw over-like) vaporizers are subject to imprecise anesthetic delivery when internal vaporizer pressure fluctuates, because of a process termed "anesthetic pumping". In common use, the vaporizer is open to atmosphere on the inflow side and open to the patient's airway on the outflow side. A device to ventilate the patient, such as a self-inflating ventilator bag, is often inserted between the vaporizer and the patient. If there is no valve between the vaporizer and the bag, pressure may be transmitted backward, compressing gas in the anesthetic chamber and bypass line. This causes additional anesthetic to leave the vaporizer retrograde or mixes it into the bypass line. In either case, on the patient's next inspiratory breath or upon re-inflation of the bag, anesthetic from the bypass line mixes with anesthetic from the anesthetic chamber raising the concentration of anesthetic administered to the patient. Because anesthetic concentration in the anesthetic chamber of the vaporizer is quite high for volatile anesthetics, this effect can be large. To avoid this, a check valve, which opens only in the direction of the patient, is placed between the vaporizer and the ventilator bag. Such a configuration prevents retrograde flow and "anesthetic pumping."

Figure 10:
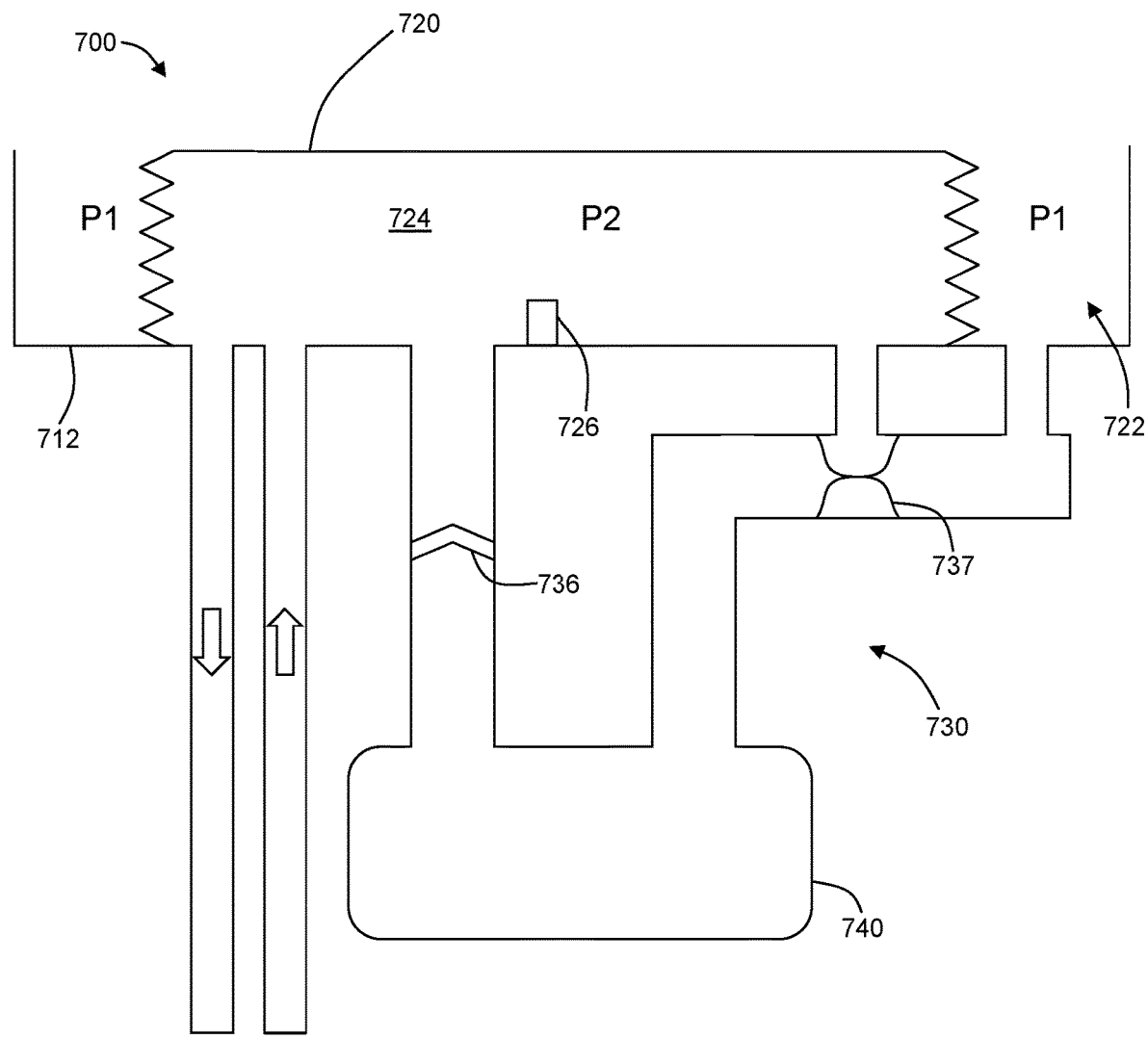
FIG. 10 depicts a portion of a rebreather where a flow path is controlled using a Starling resistor.

In some embodiments of the present disclosure, the vaporizer is exposed to fluctuating pressures at both inflow and outflow. As such, it may be desirable to guard the inflow and outflow of the vaporizer to prevent potential anesthetic pumping. FIG. 10 depicts an embodiment wherein a rebreathing device includes a conduit 730 with a check valve 736 to prevent exposure of an anesthetic chamber of the vaporizer 740 to pressure on the patient side 724 of the movable partition 720. The check valve 736 opens in the direction of bypass gas flow during delivery of gas through the vaporizer 740. On the inflow side, placement of a check valve that opens toward the actuating side 722 of the partition 720 would obstruct flow into the vaporizer 740. Accordingly, on the inflow side, the vaporizer 740 is guarded by a Starling resistor 737. The Starling resistor 737 has an internal pressure open to the actuating side 722 of the housing 712 and surrounding pressure open to the patient side 724 of the housing 712. Such a resistor 737 admits flow and transmits pressure only when the partition 720 hits the stop 726 and pressure on the patient side 724 of the device drops. At all other times during the respiratory cycle, pressure on the patient side of the partition 720 exceeds pressure on the actuating side 722 because of the weight of the bellows, both during spontaneous breathing and during positive pressure ventilation, and the Starling resistor 737 is closed. This configuration guards the vaporizer 740 from pressure changes on both inflow and outflow sides except when flow through the vaporizer 740 is required.

Figure 11:
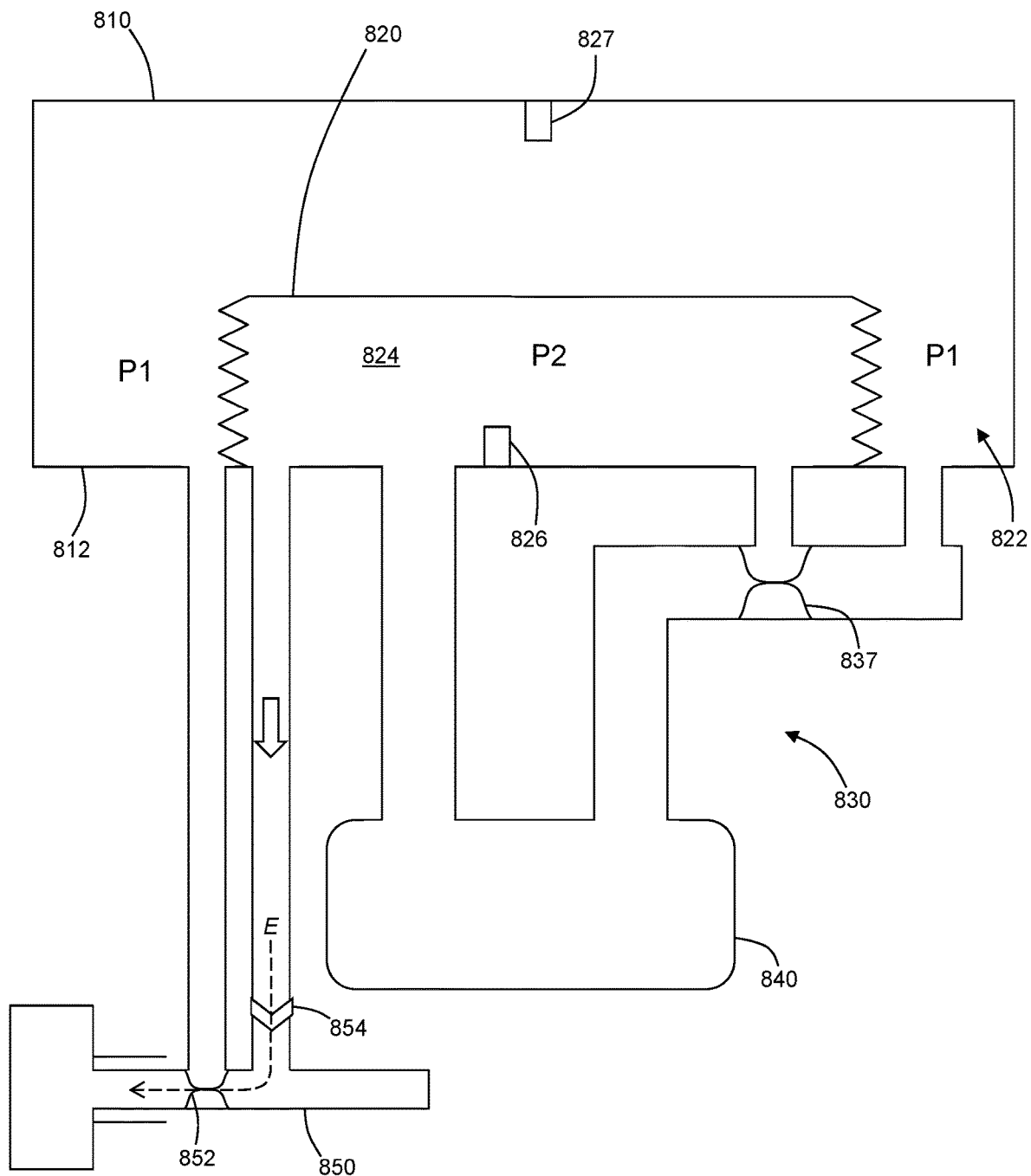
FIG. 11 depicts a rebreather having an exhaust flow path controlled by a Starling resistor.

A similar mechanism may be employed to allow an exhaust flow from the patient side of a rebreathing device (Positive end-expiratory pressure or PEEP) at pressure regulated by the ventilator. Patient expired air which has traversed the primary vaporizer of the anesthesia machine, crosses a carbon dioxide scrubber and enters the patient side 824 of the device 800. FIG. 11 depicts a rebreathing device 800 with an inflow of fresh gas at all times to the patient side 824. The fresh gas flow may be, for example, between 0.5 and 5 liters per minute. In some embodiments, this flow is between 0.5 and 2.5 liters per minute. Were some of the inflowing gas not exhausted, the bellows 820 would swell and rise to hit an upper "stop" 827. Patient side (824) pressure would then rise and prevent patient exhalation into the patient side 824 of the housing.

For this reason, the exemplary rebreathing device 810 depicted in FIG. 11 comprises an exhaust conduit 850 defining an exhaust flow path (identified as 'E'). The exhaust conduit 850 includes a Starling resistor 852 disposed in the exhaust flow path. The Starling resistor 852 has an internal channel connected to the patient side 824 of the housing 812 and a surrounding pressure connected to the actuating side 822 of the housing 812. In some embodiments, an exhaust valve 854 is provided in the exhaust flow path. Exhaust valve 854 may be biased to open only when a pressure drop across the exhaust valve 854 exceeds the partition pressure (the pressure differential caused by a weight of the moveable partition 820). In this way, the exhaust valve 854 will open only when movement of the partition 820 is prevented by an actuating side stop 827. For example, inflow to the exhaust conduit 850 can be guarded by an exhaust valve 854 requiring a pressure drop (k) across the exhaust valve for the valve to open. k is chosen to prevent the exhaust valve 854 from opening before pressure on the patient side 824 of the device 810 exceeds the pressure on the actuating side 822 by more than the partition pressure. This occurs only when the partition 820 abuts an actuating-side stop 827 and expiration continues, powered by thoracic recoil. k can be set to be, for example, slightly greater than the weight of the partition divided by its area (the "partition pressure" further described above). Otherwise, the exhaust valve would be open throughout the respiratory cycle, creating a massive leak, and the patient would not be ventilated by the device.

In this way, exhaust gas flow through the exhaust conduit 850 is permitted only when the partition 820 abuts the upper stop 827, and the pressure at which exhaust gas flow occurs is regulated by the positive end-expiratory pressure (PEEP) system of any valve or ventilator adapted to the actuating side 822 of the device 810. Patient PEEP would then exceed ventilator set PEEP by k cm $H_2O$, where k may be as low as 1 cm $H_2O$.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A rebreathing device, comprising:
   a movable partition having an actuating side on a first side of the movable partition, and a patient side on a second side of the movable partition;
   a housing disposed about the movable partition, the housing having a ventilator orifice for pneumatic communication between a ventilator and the actuating side, and having a patient orifice for pneumatic communication between the patient side and a patient; and
   a shunt defining a bypass flow path from the actuating side to the patient side, wherein the shunt is blocked during normal operation and unblocked to allow fluid flow from the actuating side to the patient side when the patient side is maximally evacuated and the moveable partition is at a maximal displacement toward the patient side.

2. The rebreathing device of claim 1, further comprising a vaporizer disposed in the bypass flow path of the shunt.

3. The rebreathing device of claim 1, further comprising a vaporizer comprising a fresh gas orifice for receiving and providing fresh gas to the patient side.

4. The rebreathing device of claim 3, wherein the bypass flow path of the shunt further comprises a $CO_2$ scrubber and a patient return orifice is in pneumatic communication with the patient side by way of the $CO_2$ scrubber.

5. The rebreathing device of claim 1, wherein the shunt comprises a valve disposed in the bypass flow path to prevent fluid flow from the patient side to the actuating side.

6. The rebreathing device of claim 5, wherein the valve is a check valve configured to allow flow when a pressure drop across the check valve exceeds a threshold value.

7. The rebreathing device of claim 5, wherein the valve is a starling resistor configured to permit fluid flow to a vaporizer when a pressure on the patient side is less than a pressure on the actuating side.

8. The rebreathing device of claim 7, wherein the shunt further comprises a check valve disposed in the bypass flow path between the vaporizer and the patient side.

9. The rebreathing device of claim 1, wherein the shunt comprises a flow meter.

10. The rebreathing device of claim 1, wherein the shunt comprises a flow alarm.

11. The rebreathing device of claim 10, wherein the flow alarm is a whistle.

12. The rebreathing device of claim 1, wherein the bypass flow path of the shunt comprises a $CO_2$ scrubber and a patient return orifice is in pneumatic communication with the patient side by way of the $CO_2$ scrubber.

13. The rebreathing device of claim 1, further comprising an exhaust conduit defining an exhaust flow path from the patient side, the exhaust conduit having a starling resistor configured to permit an exhaust flow from the patient side when a pressure on the patient side is greater than a sum of a pressure on the actuating side and a partition pressure caused by the movable partition.

14. The rebreathing device of claim 13, wherein the exhaust conduit further includes an exhaust valve disposed in the exhaust flow path between the patient side and the starling resistor, wherein the exhaust valve is configured to permit an exhaust gas flow when a pressure drop across the exhaust valve is greater than the partition pressure.

15. The rebreathing device of claim 1, wherein the movable partition is configured so as to increase a pressure within the patient side of the housing.

16. The rebreathing device of claim 15, wherein the movable partition has a weight configured to increase the pressure within the patient side of the housing.

17. A method for leak compensation in a rebreather, comprising:
   providing a rebreathing device having a movable partition for causing a gas flow in a patient side of the rebreathing device in response to a gas flow on an actuating side of the rebreathing device;
   providing the gas flow on the actuating side to cause displacement of the moveable partition towards the patient side thereby causing a gas flow from the patient side;
   causing a bypass gas flow from the actuating side to the patient side, bypassing the moveable partition, if the moveable partition reaches a maximum displacement towards the patient side and preventing the bypass gas flow if the moveable partition is not maximally displaced towards the patient side; and
   providing an anesthetic vaporizer disposed in the bypass gas flow for providing anesthetic to the patient.

* * * * *